US012747195B2

(12) United States Patent
Iida et al.

(10) Patent No.: US 12,747,195 B2
(45) Date of Patent: Sep. 29, 2026

(54) OLIGOMERIZATION WITH ION-EXCHANGED ZEOLITES

(71) Applicant: EXXONMOBIL TECHNOLOGY AND ENGINEERING COMPANY, Annandale, NJ (US)

(72) Inventors: Takayuki Iida, Iselin, NJ (US); Michael A. Marella, Easton, PA (US); Suzzy C. Ho, Princeton, NJ (US); Gerardo J. Majano, Basking Ridge, NJ (US); Michael P. Lanci, Flemington, NJ (US); Trong Pham, Flemington, NJ (US)

(73) Assignee: EXXONMOIL TECHNOLOGY AND ENGINEERING COMPANY, Spring, TX (US)

( * ) Notice: Subject to any disclaimer, the term of this patent is extended or adjusted under 35 U.S.C. 154(b) by 241 days.

(21) Appl. No.: 18/649,059

(22) Filed: Apr. 29, 2024

(65) Prior Publication Data

US 2024/0368057 A1 Nov. 7, 2024

Related U.S. Application Data

(60) Provisional application No. 63/500,351, filed on May 5, 2023.

(51) Int. Cl.

| | |
|---|---|
| ***C07C 2/12*** | (2006.01) |
| ***B01J 29/70*** | (2006.01) |
| ***B01J 35/64*** | (2024.01) |
| ***B01J 37/30*** | (2006.01) |

(52) U.S. Cl.

CPC ............. *C07C 2/12* (2013.01); *B01J 29/7026* (2013.01); *B01J 29/7034* (2013.01); *B01J 29/7046* (2013.01); *B01J 35/643* (2024.01); *B01J 37/30* (2013.01); *B01J 2229/183* (2013.01); *C07C 2529/70* (2013.01)

(58) Field of Classification Search

CPC .... C07C 2/12; C07C 2529/70; B01J 29/7026; B01J 29/7034; B01J 29/7046; B01J 35/643; B01J 37/30; B01J 2229/183; C10G 50/00

USPC .......................................................... 585/533

See application file for complete search history.

(56) References Cited

U.S. PATENT DOCUMENTS

| | | | |
|---|---|---|---|
| 4,873,067 | A | 10/1989 | Valyocsik et al. |
| 5,234,875 | A | 8/1993 | Han et al. |
| 5,284,989 | A | 2/1994 | Apelian et al. |
| 5,405,596 | A | 4/1995 | Moini et al. |

(Continued)

*Primary Examiner* — Prem C Singh
*Assistant Examiner* — Francis C Campanell
(74) *Attorney, Agent, or Firm* — Shook Hardy & Bacon L.L.P.

(57) ABSTRACT

Catalysts and corresponding methods for oligomerization of olefins to distillate boiling range compounds are provided. The oligomerization can be performed in the presence of a catalyst including a 10-member ring or 1-D 12-member ring zeolitic framework material that contains both silica and alumina. The zeolitic framework material can have a low molar ratio of silica to alumina. The zeolitic framework material can be ion-exchanged to a small but substantial degree with alkaline earth metal cations, such as Mg, Ca, Sr, or Ba. The small but substantial amount of ion exchange can correspond to having a molar ratio of alkaline earth metal to aluminum of up to 0.2.

18 Claims, 7 Drawing Sheets

(56) References Cited

U.S. PATENT DOCUMENTS

| | | | |
|---|---|---|---|
| 6,143,942 A | 11/2000 | Verrelst et al. | |
| 6,893,624 B2 | 5/2005 | Lai et al. | |
| 8,500,991 B2 | 8/2013 | Lai et al. | |
| 8,901,363 B2 | 12/2014 | Corma et al. | |
| 2011/0282123 A1* | 11/2011 | Corma | B01J 37/30<br>585/533 |

* cited by examiner

OLIGOMERIZATION WITH ION-EXCHANGED ZEOLITES

CROSS-REFERENCE TO RELATED APPLICATION

This non-provisional patent application claims priority to U.S. provisional patent app. No. 63/500,351, filed May 5, 2023, and titled "Oligomerization With Ion-Exchanged Zeolites," the entire contents of which is incorporated herein by reference.

FIELD OF THE INVENTION

Zeolitic catalysts are provided that have improved activity and selectivity for oligomerization, along with corresponding systems and methods.

BACKGROUND OF THE INVENTION

Oligomerization of light olefins is one potential pathway for forming liquid fuels derived from bio-derived sources and/or other alternative sources. For example, one option for forming liquid fuels from biomass is to first convert the biomass to alcohols (such as via a syngas intermediate). Such alcohols can then be converted to olefins for oligomerization.

When attempting to form compounds for use in a diesel fuel, a variety of factors need to be balanced. First, achieving a high yield of diesel boiling range compounds is desirable. Another consideration that is at least indirectly related to yield is avoiding cracking of the resulting diesel boiling range compounds. Still another consideration can be reducing or minimizing coking. Additionally, the cetane rating for compounds tends to decrease with branching, so controlling the branching of the resulting diesel boiling range compounds is also desirable.

What is needed are catalysts that can provide further improvements when oligomerizing olefins to form diesel boiling range compounds.

U.S. Pat. No. 5,234,875 describes coke-selectivated porous acidic crystalline catalysts for use in oligomerization. ZSM-23 is described as an example of this type of coke-selectivated catalyst.

U.S. Pat. Nos. 5,284,989 and 6,143,942 provide additional examples of performing oligomerization using acidic zeolitic catalysts.

U.S. Pat. No. 5,405,596 describes methods for synthesis of ZSM-23.

U.S. Pat. No. 8,500,991 describes small particle size ZSM-23 crystals.

U.S. Pat. No. 6,893,624 describes methods for synthesis of ZSM-12 crystals.

U.S. Pat. No. 4,873,067 describes methods for synthesis of ZSM-57 crystals.

U.S. Pat. No. 8,901,363 describes an alkene oligomerization process. The oligomerization is performed using a zeolitic catalyst that is partially neutralized using alkali metal cations or alkaline earth metal cations. The examples show using alkali metal cations to neutralize 10% or more of the acidic sites on a TON zeolitic framework catalyst to provide an oligomerization catalyst that has improved retention of catalytic activity over time. However, the examples also show that selectivity improvement is limited, as only the examples including sodium as the alkali metal cation show an improvement in diesel selectivity. When only the heavier potassium cation was used, the selectivity for diesel was either similar to or less than the selectivity of the catalyst in H-form.

SUMMARY

In an aspect, a method for oligomerizing olefins is provided. The method includes exposing a feed comprising $C_2$ to $C_{12}$ olefins to an oligomerization catalyst including an alkaline earth metal ion-exchanged zeolitic framework material under oligomerization conditions to form an oligomerized effluent including a diesel boiling range fraction. The alkaline earth metal ion-exchanged zeolitic framework material can contain silica and alumina. The alkaline earth metal ion-exchanged zeolitic framework material can have a molar ratio of alkaline earth metals to aluminum of 0.005 to 0.2. The alkaline earth metal ion-exchanged zeolitic framework material can include a 10-member ring zeolitic framework structure, a 1-D 12-member ring zeolitic framework structure, or a combination thereof.

DETAILED DESCRIPTION

Overview

Figure 1:
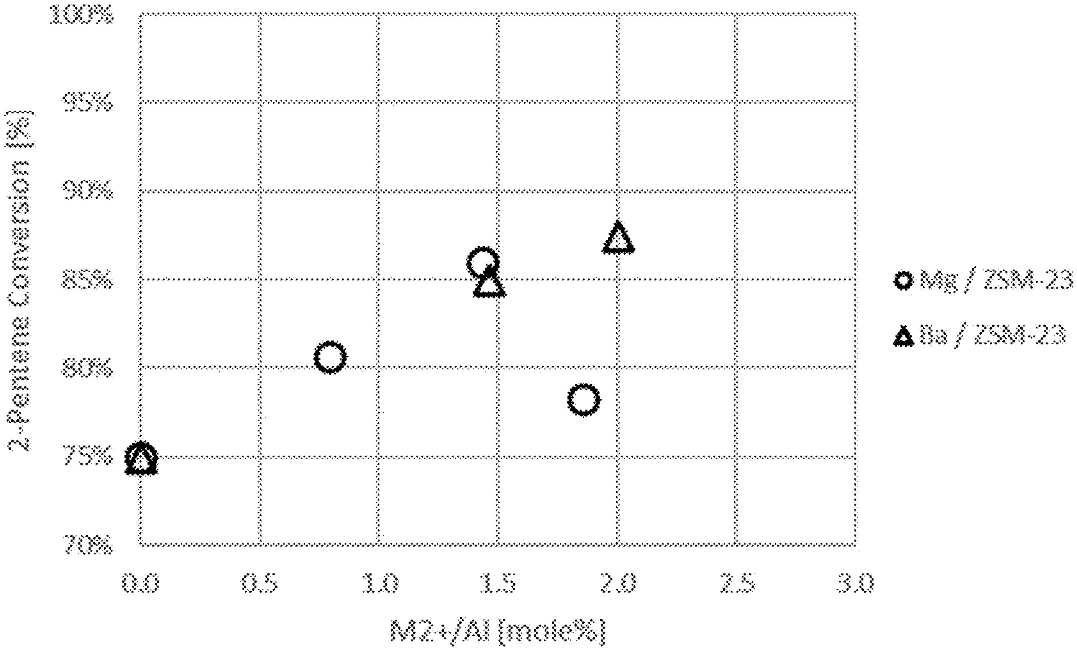
FIG. 1 shows olefin conversion during oligomerization reactions using ZSM-23 catalysts with various amounts of alkaline earth metal ion exchange.

In various aspects, catalysts and corresponding methods for oligomerization of olefins to distillate boiling range compounds, such as diesel boiling range compounds, are provided. The oligomerization can be performed in the presence of a 10-member ring or 1-D 12-member ring zeolitic framework material that contains both silica and alumina. The zeolitic framework material can have a low molar ratio of silica to alumina. Additionally, the zeolitic framework material can be ion-exchanged to a small but substantial degree with alkaline earth metal cations, such as Mg, Ca, Sr, or Ba. The small but substantial amount of ion exchange can correspond to having a molar ratio of alkaline earth metal to aluminum of up to 0.2. However, it has been unexpectedly discovered that the benefits of ion exchange with alkaline earth metal cations can be at least partially realized with molar ratios of alkaline earth metal to aluminum of 0.005 to 0.08, or 0.005 to 0.05. The benefits of using a 10-member ring or 1-D 12-member ring zeolitic framework material that is ion-exchanged with a small but substantial amount alkaline earth metals include, but are not limited to, improved selectivity for formation of distillate and/or or diesel boiling range compounds as well as improved ability to maintain catalytic activity over time.

Conventionally, a variety of different types of zeolitic framework materials have been used as oligomerization catalysts. Common difficulties with performing oligomerization to make diesel boiling range compounds include loss of catalytic activity over time and low selectivity for production of the diesel boiling range compounds.

Ion exchange of zeolitic framework materials is conventionally performed in a variety of contexts. Typically, when ion exchange is performed to convert to associate cations other than hydrogen with aluminum sites in the zeolitic framework material, the amount of ion exchange is substantial relative to the amount of aluminum in the framework. As a result, zeolitic framework materials that are ion-exchanged typically have molar ratios of cations to alumina of 0.1 or more (i.e., roughly 10 mol % or more of the aluminum atoms in the zeolitic framework material are associated with a cation different from hydrogen).

It has been unexpectedly discovered that benefits during oligomerization can be realized by performing ion exchange on certain types of zeolitic framework materials at lower than typical levels. In particular, it has been discovered that performing ion exchange on 10-member ring and/or 1-D 12-member ring zeolitic framework materials with alkaline earth metal cations in a cation to aluminum molar ratio of 0.005 to 0.08 provides benefits for both maintaining oligomerization activity over time as well as improving selectivity for production of distillate and/or diesel boiling range compounds.

Without being bound by any particular theory, it is believed that alkaline earth metal cations can preferentially associate with ion-exchange locations in a zeolitic framework material that have a +2 nominal charge (i.e., locations where two aluminum atoms are in relatively close proximity). These locations are believed to be higher in acidity. By associating a small but substantial amount of an alkaline earth metal cation with a zeolitic framework material, these higher acidity locations can be preferentially associated with the exchanged ions. This is believed to assist with improving selectivity to higher boiling range compounds, as the potential for cracking of longer chain compounds in the presence of the zeolitic framework material is reduced.

In some aspects, the benefits of incorporating a small but substantial amount of alkaline earth metal into a 10-member ring and/or 1-D 12-member ring zeolitic framework material can be more pronounced for zeolitic framework materials with a relatively low molar ratio of silica to alumina (or equivalently a low molar ratio of Si to $Al_2$). For zeolitic framework materials with high silicon contents relative to the amount of aluminum in the zeolitic framework, the number of instances where two Al atoms will be at adjacent sites and/or in sites with close proximity will be relatively low. As the molar ratio of silica to alumina decreases, and therefore the alumina content of the zeolitic framework increases, the number of potential divalent sites where Al atoms are adjacent and/or in close proximity can increase. In some aspects, the molar ratio of silica to alumina in a zeolitic material can be 100 or less, or 70 or less, or 60 or less, or 50 or less, such as down to 10 or possibly still lower. In some optional aspects, the zeolitic framework can include 1.0 wt % or less of phosphorus. Generally, the silica content of the zeolitic framework material can be greater than the alumina content.

Definitions

In this discussion, a zeolitic framework material is defined to refer to a crystalline material having a porous framework structure built from tetrahedra atoms connected by bridging oxygen atoms. Examples of known zeolitic framework structures (or materials) are given in the "Atlas of Zeolite Frameworks" published on behalf of the Structure Commission of the International Zeolite Association", 6th revised edition, Ch. Baerlocher, L. B. McCusker, D. H. Olson, eds., Elsevier, New York (2007) and the corresponding web site, http://www.iza-structure.org/databases/. Under this definition, a zeolite refers specifically to an aluminosilicate having a zeolitic framework structure. Under this definition, a zeolitic material or a zeolitic framework material can refer to aluminosilicates (i.e., zeolites) as well as crystalline structures containing oxides of heteroatoms different from silicon and aluminum. Such heteroatoms can include any heteroatom generally known to be suitable for inclusion in a zeotype framework, such as gallium, boron, germanium, phosphorus, zinc, and/or other transition metals that can substitute for silicon and/or aluminum in a zeolitic framework. It is noted that under this definition, a zeolitic framework material can include materials such as silicoaluminophosphate (SAPO) materials or aluminophosphate (AIPO) materials.

The framework of zeolites (or molecular sieves) are commonly characterized in terms of their ring size, wherein the ring size refers to the number of tetrahedra atoms (e.g., Si, Al, or alternative atoms) that are tetrahedrally coordinated with oxygen atoms in a loop to define a pore or channel within the interior of the zeolite. For example, an "8-ring" zeolite refers to a zeolite having pores or channels defined by 8 alternating tetrahedral atoms and 8 oxygen atoms in a loop. The pores or channels defined within a given zeolite may be symmetrical or asymmetrical depending upon various structural constrains that are present in the particular framework. Zeolites can be classified as having small, medium, large, and extra-large pore structures for pore windows delimited by 8, 10, 12, and more than 12 T-atoms, respectively. Extra-large pore zeolites (>12R) include, for example, AET (14R, e.g., ALPO-8), SFN (14R, e.g., SSZ-59), VFI (18R, e.g., VPI-5), CLO (20R, e.g., cloverite), and ITV (30R, e.g., ITQ-37) framework type zeolites. Extra-large pore zeolites generally have a free pore diameter of larger than about 0.8 nm. Large pore zeolites (12R) include, for example, LTL, MAZ, FAU, EMT, OFF, MTW, *BEA, MOR, and SFS framework type zeolites, e.g., mazzite, offretite, zeolite L, zeolite Y, zeolite X, omega, ZSM-2, ZSM-12, zeolite T, Beta, and SSZ-56. Large pore zeolites generally have a free pore diameter of 0.6 to 0.8 nm. Medium (or intermediate) pore size zeolites (10R) include, for example, MFI, MEL, *MRE, EUO, MTT, MFS, AEL, AFO, HEU, FER, MWW, and TON framework type zeolites, e.g., ZSM-5, ZSM-11, ZSM-48, ZSM-22, ZSM-23, ZSM-35, MCM-22, silicalite-1, and silicalite-2. Medium pore size zeolites generally have a free pore diameter of 0.45 to 0.6 nm. Small pore size zeolites (8R) include, for example, CHA, RTH, ERI, KFI, LEV, and LTA framework type zeolites, e.g., ZK-4, SAPO-34, SAPO-35, ZK-14, SAPO-42, ZK-21, ZK-22, ZK-5, ZK-20, zeolite A, chabazite, and ALPO-17. Small pore size zeolites generally have a free pore diameter of 0.3 to 0.45 nm.

The Alpha value is a measure of the cracking activity of a catalyst and is described in U.S. Pat. No. 3,354,078 and in the Journal of Catalysis, Vol. 4, p. 527 (1965); Vol. 6, p. 278 (1966) and Vol. 61, p. 395 (1980), each incorporated herein by reference. It is based on the activity of the active silica-alumina cracking catalyst taken as an Alpha of 1 (Rate Constant=0.016 $sec^{-1}$). The experimental conditions of the test used herein included a constant temperature of 538° C. and a variable flow rate as described in detail in the Journal of Catalysis, Vol. 61, p. 395 (1980).

In this discussion, the composition of a zeolite can be characterized using ICP-AES (Inductively Coupled Plasma Atomic Emission Spectroscopy).

In this discussion, surface areas correspond to Brunauer-Emmett-Teller (BET) specific surface areas determined by the BET method as described by S. Brunauer, P. H. Emmett and E. Teller, J. Am. Chem. Soc., 1938, 60, 309, incorporated herein by reference for the limited purpose of describing the BET method, based on $N_2$ adsorption-desorption at liquid nitrogen temperature. The micropore volume was measured with nitrogen physisorption, and the data can be analyzed by the t-plot method described in Lippens, B. C. et al., "Studies on pore system in catalysts: V. The t method", J. Catal., 4, 319 (1965), which describes micropore volume methods and is incorporated herein by reference for the limited purpose of describing micropore volume methods.

In this discussion, acidity is determined based on temperature programmed ammonia desorption (TPAD).

In this discussion, "Tx" refers to the temperature at which a weight fraction "x" of a sample can be boiled or distilled. For example, if 40 wt % of a sample has a boiling point of 350° F. (177° C.) or less, the sample can be described as having a T40 distillation point of 350° F. (177° C.).

In this discussion, the diesel boiling range is defined as 177° C. (350° F.) to 371° C. A fraction that has a T10 distillation point of 177° C. or more and a T90 distillation point of 371° C. or less is defined as a distillate boiling range fraction. In this discussion, the distillate boiling range is defined as 160° C. (320° F.) to 371° C. A fraction that has a T10 distillation point of 160° C. or more and a T90 distillation point of 371° C. or less is defined as a distillate boiling range fraction. The naphtha boiling range is defined as the boiling point of a $C_5$ paraffin (roughly 29° C.) to 177° C. A fraction having a T10 boiling point of 29° C. or more and a T90 distillation point of 177° C. or less is defined as a naphtha boiling range fraction. It is noted that the T10 distillation point of a fraction must be equal to or less than the T90 distillation point, and that similarly the T90 distillation point of a fraction must be equal to or greater than the T10 distillation point. The distillation profile of a fraction, feed, or product is determined according to ASTM D2887. For a sample where ASTM D2887 is not appropriate for some reason, D86 (for lower boiling fractions) or D7169 (higher boiling fractions) may be used instead.

Unless otherwise specified, the "Liquid Hourly Space Velocity (LHSV)" for a feed or portion of a feed to a reactor is defined as the volume of feed per hour relative to the volume of catalyst in the reactor. In some specific instances, a liquid hourly space velocity may be specified relative to a specific catalyst within a reactor that contains multiple catalyst beds.

In this discussion, a "Cx" hydrocarbon refers to a hydrocarbon compound that includes "x" number of carbons in the compound. A stream containing "Cx-Cy" hydrocarbons refers to a stream composed of one or more hydrocarbon compounds that includes at least "x" carbons and no more than "y" carbons in the compound. It is noted that a stream containing "Cx-Cy" hydrocarbons may also include other types of hydrocarbons, unless otherwise specified.

In this discussion, references to a "gas portion" or a "liquid portion" of a reaction effluent refer to the phase the effluent portion would be in at 20° C. and 100 kPa-a. In this discussion, references to a "gas phase portion" or a "liquid phase portion" of a reaction effluent refer to the phase the effluent portion is in at the specified conditions. For example, a "gas phase portion" of a hydrocracking effluent as the effluent exits from the reactor would refer to the portion of the hydrocracking effluent that is in the gas phase under the conditions present at the exit from the hydrocracking reactor. This could include compounds that boil at up to 400° C. or more, depending on the temperature at the exit from the hydrocracking reactor. By contrast, the "gas portion" of such a hydrocracking effluent would only correspond to the components of the effluent that are gas phase at 20° C. and 100 kPa-a, such as $C_{4-}$ hydrocarbons, carbon oxides, hydrogen, $H_2S$, and other low boiling compounds.

In this discussion, references to a periodic table are defined as references to the current version of the IUPAC Periodic Table.

Oligomerization Catalyst

In some aspects, an oligomerization catalyst can correspond to or include a 10-member ring zeolitic framework material that is ion-exchanged with an alkaline earth metal cation in a small but substantial amount. The 10-member ring zeolitic framework material can have a 1-D, 2-D, or 3-D pore structure.

In other aspects, an oligomerization catalyst can correspond to or include a 12-member ring zeolitic framework material that is ion-exchanged with an alkaline earth metal cation in a small but substantial amount. The 12-member ring zeolitic framework material can have a 1-D pore structure. In still other aspects, an oligomerization catalyst can correspond to an intergrowth material of 10-member ring and/or 12-member ring zeolitic framework materials.

In some aspects, the zeolitic framework material can correspond to a 1-D zeolitic framework material having the framework structure of MTT (e.g., ZSM-23), MTW (e.g., ZSM-12), *MRE (e.g., ZSM-48), EUO (e.g., EU-1), TON (e.g., ZSM-22, Theta-1), or a combination thereof. In some aspects, the 1-D zeolitic framework material can correspond to a material having the framework structure of MTT, MTW, *MRE, or a combination thereof. In some aspects, the zeolitic framework material can correspond to a material having the framework structure MTT. Methods for synthesis of various types of zeolitic frameworks is generally known. As an example, ZSM-23 can be synthesized according to the methods described in U.S. Pat. No. 8,500,991.

In some aspects, the zeolitic framework material can correspond to a 2-D or 3-D 10-member ring zeolitic framework material. In such aspects, the framework structure can correspond to FER (e.g., ZSM-35), MFS (e.g., ZSM-57), MFI (e.g., ZSM-5), MEL, or a combination thereof. In some aspects, the framework structure can correspond to MFS, MFI, or a combination thereof. In some aspects, the framework structure can correspond to MFI, MEL, or a combination thereof.

It is noted that combinations of framework structures can include intergrowth materials, such as an intergrowth material corresponding to an intergrowth of MEL framework and MFI framework. ZSM-11 is an example of this type of intergrowth material. It is further noted that some older sources may refer to ZSM-11 as an MEL framework material. However, more recent characterizations have found that aluminosilicate ZSM-11 is actually an intergrowth of MFI and MEL.

Another option for specifying the pore channel size of a zeolitic framework material is based on the pore size in Angstroms. In some aspects, the zeolitic framework structure can have a pore size of 4.5 Angstroms to 8.0 Angstroms, or 5.0 Angstroms to 8.0 Angstroms, or 4.5 Angstroms to 7.0 Angstroms, or 5.0 Angstroms to 7.0 Angstroms, or 4.5 Angstroms to 6.0 Angstroms, or 5.0 Angstroms to 6.0 Angstroms, or 4.5 Angstroms to 5.6 Angstroms.

A 10-member ring and/or 12-member ring zeolitic material can then be ion-exchanged to achieve a small but substantial loading of alkaline earth metal cations. Suitable alkaline earth metal cations may be selected from the group consisting of calcium, magnesium, strontium, barium, and mixtures thereof, preferably magnesium and/or barium. The ion-exchange process to achieve a small but substantial loading of alkaline earth metal cations may be conducted by any conventional ion-exchange method known in the art. For instance, the ion-exchange process may comprise exposing the zeolitic framework material to a source of the alkaline earth metal cations, such as a solution comprising an alkaline earth metal salt, under conditions sufficient to exchange some of the aluminum in the zeolitic framework material with said alkaline earth metal cations. Suitable alkaline earth metal salts include sulfate, nitrate, chloride and/or acetate of the alkaline earth metal, e.g., alkaline earth metal nitrates. For example, the zeolitic framework material may be ion-exchanged by contacting with a solution, e.g., an aqueous solution, of the alkaline earth metal sulfate, nitrate, chloride and/or acetate. Contacting may be performed at room temperature or by heating, e.g., in a sealed autoclave in a convention oven at 100° C. or at boiling temperature in an open system. The ion-exchanged zeolitic framework may then be recovered by filtration and washed with deionized water, and dried.

The ion-exchange with alkaline earth metal cations may take place by contacting the source of the alkaline earth metal cations with the zeolitic framework material in any suitable form, such as in its as-synthesized form, H-form, ammonium-form, and possibly whether before and/or after calcination and/or extrusion. In some aspects, the ion-exchange with alkaline earth metal cations can be achieved by performing ion exchange on an H-form zeolitic material. In other aspects, this can be achieved by first converting the zeolitic material to ammonium form, e.g., after an ion-exchange treatment with aqueous ammonium salts, such as ammonium nitrate, ammonium chloride, and ammonium acetate, and then performing ion exchange with alkaline earth metal cations on the ammonium form. In still other aspects, any convenient starting point can be used so long as the resulting material has a molar ratio of alkaline earth metal cations to aluminum atoms of 0.005 to 0.2, or 0.005 to 0.08, or 0.005 to 0.05, or 0.005 to 0.02.

Optionally, the oligomerization catalyst may be in the form of a product composition comprising the zeolitic framework material of the present disclosure in combination with other materials, such as binders and/or matrix materials that provide additional hardness to the finished product. These other materials can be inert or catalytically active materials. For instance, it may be desirable to incorporate the zeolitic framework material of the present disclosure with another material that is resistant to the temperatures and other conditions employed during use. Such materials include synthetic or naturally occurring zeolites as well as inorganic materials such as clays, silica and/or metal oxides such as alumina and mixtures thereof. The metal oxides may be either naturally occurring or in the form of gelatinous precipitates or gels including mixtures of silica and metal oxides. Use of a resistant material in conjunction with the molecular sieve of the present disclosure, i.e., combined therewith or present during synthesis of the as-made zeolitic material, which crystal is active, tends to change the conversion and/or selectivity of the catalyst in certain organic conversion processes. Inactive resistant materials suitably serve as diluents to control the amount of conversion in a given process so that products can be obtained in an economic and orderly manner without employing other means for controlling the rate of reaction. These materials may be incorporated into naturally occurring clays, e.g., bentonite and kaolin, to improve the crush strength of the product under commercial operating conditions. Said inactive resistant materials, i.e., clays, oxides, etc., function as binders for the catalyst. A catalyst having good crush strength can be beneficial because in commercial use, it is desirable to prevent the catalyst from breaking down into powder-like materials. Naturally occurring clays which may be used include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or after being subjected to calcination, acid treatment or chemical modification. Examples of suitable inorganic oxide binders include, but are not limited to, silica, alumina, silica-alumina, titania, zirconia, magnesia, beryllia, yttria, gallium oxide, zinc oxide and mixtures thereof. In addition to the foregoing materials, the zeolitic framework material of the present disclosure may be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

These binder materials are resistant to the temperatures and other conditions, e.g., mechanical attrition, which occur in various hydrocarbon separation processes. Thus the zeolitic framework material of the present disclosure may be used in the form of an extrudate with a binder. They are typically bound by forming a pill, sphere, or extrudate. The extrudate is usually formed by extruding the zeolitic framework material, optionally in the presence of a binder, and drying and calcining the resulting extrudate. Further treatments such as steaming, and/or ion exchange may be carried out as required. When mixed with a binder and extruded to form catalyst particles, the catalyst particles can include 10 wt % to 99 wt % of the oligomerization catalyst and 1.0 wt % to 90 wt % binder, or 10 wt % to 90 wt % binder, or 25 wt % to 75 wt % binder. The zeolitic framework material and binder may be composited by, for example, intimately mixing them together in the presence of water, and extruding or otherwise shaping, e.g., by pelletizing.

The oligomerization catalyst can be used to oligomerize an olefin-containing feed. The olefins for oligomerization can correspond to olefins containing 2 to 12 carbon atoms, or 2 to 6 carbon atoms. Optionally, the olefin-containing feed can contain propene, n-butene, isobutene, one or more pentenes, or a combination thereof. The olefin-containing feed can further contain one or more diluents, such as saturated hydrocarbons or $N_2$. For example, a feed containing propene or another olefin can optionally further contain the corresponding alkane, such as propane. In such an example, the weight ratio of alkene to alkane can be between 10:90 to 90:10, or between 20:80 to 60:40, or between 30:70 to 70:30. In some aspects, the weight ratio of $C_2$-$C_{12}$ alkenes to $C_2$-$C_{12}$ alkanes can be between 10:90 to 90:10, or between 20:80 to 60:40, or between 30:70 to 70:30. In some aspects, the weight ratio of $C_2$-$C_6$ alkenes to $C_2$-$C_6$ alkanes can be between 10:90 to 90:10, or between 20:80 to 60:40, or between 30:70 to 70:30. Optionally, the olefin-containing feed can further contain water vapor.

In various aspects, oligomerization can be performed in a reaction environment having a temperature of 170° C. to 300° C., or 170° C. to 260° C., or 180° C. to 260° C. Additionally or alternately, the pressure in the reaction environment can be 5.0 MPa-a to 10 MPa-a, or 6.0 MPa-a to 8.0 MPa-a. Further additionally or alternately, the oligomerization can be performed at an olefin weight hourly space velocity of 0.1 $hr^{-1}$ to 20 $hr^{-1}$, or 1.0 $hr^{-1}$ to 10 $hr^{-1}$, or 1.5 $hr^{-1}$ to 7.5 $hr^{-1}$.

In various aspects, oligomerization using a catalyst including an alkaline earth metal ion-exchanged zeolitic framework material can be performed with a conversion rate of olefins in the feed of 70% or more, or 75% or more, or 80% or more, such as up to 100% conversion of the olefins in the feed to higher boiling point compounds.

Zeolitic framework materials that are ion exchanged with a small but substantial amount of alkaline earth metal cations can provide improved selectivity for production of diesel. One method for characterizing this improved selectivity is based on the molar ratio of $C_{11+}$ hydrocarbons in the oligomerized product relative to the amount of $C_{9+}$ hydrocarbons. For example, when performing oligomerization with a feed based primarily on pentenes, the ratio of $C_{11+}$ hydrocarbons versus $C_{9+}$ hydrocarbons provides an indication of the amount of oligomerized hydrocarbons based on the combining of three or more pentenes versus the amount of hydrocarbons that underwent some type of cracking in the oligomerization environment. In some aspects, the molar ratio of $C_{11+}$ hydrocarbons to $C_{9+}$ hydrocarbons can be increased by 5% or more when using an oligomerization catalyst including a zeolitic framework material having a molar ratio of alkaline earth metals to aluminum of 0.005 to 0.2, or 0.005 to 0.08, or 0.005 to 0.05, or 0.005 to 0.02. This increase is relative to the ratio achieved under the same conditions when using the corresponding oligomerization catalyst without any alkaline earth metal content.

Synthesis of Ion-Exchanged Zeolitic Framework Materials

The zeolitic framework materials as described herein, useful as oligomerization catalysts, can be synthesized according to conventional methods prior to performing the small but substantial amount of ion exchange with an alkaline earth metal.

As an example, ZSM-23 can be prepared according to the method described in Example 1 of U.S. Pat. No. 8,500,991. It is noted that the structure directing agent in this synthesis is "Triquat-7", but other convenient types of structure directing agents could be used. Triquat-7 has the following formula:

$$(CH_3)_3N^+CH_2CH_2CH_2N^+(CH_3)_2CH_2CH_2CH_2N^+(CH_3)_3 \quad (1)$$

To make ZSM-23, a mixture was prepared from 975 g of water, 75 g of Triquat-7 40% solution, 180 g of Ludox HS-40 colloidal silica, 10.8 g of sodium aluminate solution (45%), and 22.8 g of 50% sodium hydroxide solution. 10 g of ZSM-23 seeds ($SiO_2/Al_2O_3$ about 40/1) were then added to the mixture. The mixture had the following molar composition:

| | |
|---|---|
| $SiO_2/Al_2O_3$ | ~44 |
| $H_2O/SiO_2$ | ~53 |
| $OH^-/SiO_2$ | ~0.32 |
| $Na^+/SiO_2$ | ~0.32 |
| Triquat-7/$SiO_2$ | ~0.07 |

The mixture was reacted at 338° F. (170° C.) in a 2-liter autoclave with stirring at 250 RPM for 120 hours. The product was filtered, washed with deionized (DI) water and dried at 250° F. (120° C.). The XRD pattern of the as-synthesized material showed the typical phase of ZSM-23 topology. The SEM of the as-synthesized material showed that the material was composed of agglomerates of small crystals. The resulting ZSM-23 crystals had a $SiO_2/Al_2O_3$ molar ratio of about 41.

To form a zeolitic framework material with a small but substantial amount of ion exchange with an alkaline earth metal, zeolitic crystals (e.g., as-synthesized crystals made according to a method similar to the above) can be calcined to remove the template or structure directing agent. For example, the crystals can be calcined at 550° C. for roughly 6 hours. Ion-exchange can then be performed using 1M $NH_4NO_3$ to produce the ammonium form of the material. For example, ion exchange using ammonium nitrate can be performed three or more times to form a substantially ammonium form zeolitic material. Then, the zeolitic framework material can be mixed with solution(s) that contain various amounts of one or more alkaline earth metal salts. Examples of suitable salts include nitrate salts of Mg, Ba, Sr, and/or Ca. In some aspects, the salt can be a salt of Mg or Ca. A suitable liquid to solid ratio can be roughly 10 mL/1 g, although other ratios can be used. The exposure of the zeolitic material to the alkaline earth metal salts can be performed for an extended period, e.g., at room temperature under stirring, such as overnight. After removal from the solution, the resulting material with a small but substantial amount of alkaline earth metal ion content can be calcined prior to use and/or testing.

Example 1—Ion-Exchanged ZSM-23

Synthesis of ZSM-23 was conducted following method described in U.S. Pat. No. 8,500,991. The composition of the resulting ZSM-23 crystal product had a molar ratio of $SiO_2$ to $Al_2O_3$ of 41 according to ICP-AES (Inductively Coupled Plasma Atomic Emission Spectroscopy). The as-synthesized crystal was calcined at 550° C. for 6 hr under air to remove the template. Ion-exchange using 1M $NH_4NO_3$ was conducted three times to produce the ammonium form of the material. Then, the zeolite was mixed with solutions that contained various amounts of $Mg(NO_3)_2$ and $Ba(NO_3)_2$ for ion-exchange. The liquid to solid ratio was fixed to 10 mL/1 g, and the treatment was conducted overnight at room temperature under stirring. Finally, the material was calcined at 550° C. for 6 hr for further analyses including catalytic testings.

To evaluate the resulting ion-exchanged catalysts, roughly 10 mg of catalyst was loaded in a ~0.5 mL of small stainless steel cell (made from ⅜ inch Swagelok cap and plug). The cell and the catalyst were heated to 150° C. overnight. The cell weight plus catalyst was recorded before heating and after cooling to room temperature. Using a syringe, ~0.37 mL (~260 mg) of a solution composed of 0.6 g of 2-pentenes, 50 mg of n-undecane and 200 mL of hexane was added to the cell. The cell was sealed and its weight recorded before placing it in a furnace at 180° C. for 4 hours. An aliquot of the starting solution was also analyzed by gas chromatography. This allowed for calculation of conversion and the amount of the products formed.

Table 1 summarizes the composition, textual properties, and acid concentration of $M^{2+}$/ZSM-23 zeolites analyzed using ICP-AES, $N_2$ adsorption, and TPAD, respectively. Despite limited degree of ion-exchange ($M^{2+}$/Al<2%), significant loss in the micropore volume was observed compared to the parent material (0.106 cc/g), indicating that the alkali earths are occupying the zeolite micropores. Despite micropore volume loss, the acid concentration was maintained between 0.65 and 0.69 mEq/g except for 1.8 Mg/ZSM-23, where the value was reduced to 0.438 mEq/g. The sample names were designated based on the type of alkali earth (Mg or Ba) and the $M^{2+}$/Al molar ratio in %. The designated names are also summarized in Table 1.

TABLE 1

Characterization of ZSM-23 Ion-Exchanged Samples

| Sample name | $M^{2+}$/Al | BET specific surface area [$m^2$/g] | Micropore volume [cc/g] | Ammonia desorbed [mEq/g] |
|---|---|---|---|---|
| Parent ZSM-23 | 0.000 | 306.3 | 0.106 | 0.648 |
| 0.8 Mg/ZSM-23 | 0.008 | 303.8 | 0.105 | 0.651 |
| 1.4 Mg/ZSM-23 | 0.014 | 266.4 | 0.101 | 0.649 |
| 1.9 Mg/ZSM-23 | 0.019 | 241.3 | 0.090 | 0.430 |
| 1.5 Ba/ZSM-23 | 0.015 | 240.3 | 0.091 | 0.687 |
| 2.0 Ba/ZSM-23 | 0.020 | 309.4 | 0.106 | 0.690 |

The materials in Table 1 were tested for 2-pentene (2-C5=, cis and trans) oligomerization reaction in a batch reactor configuration. The conversion was calculated from the amount of remaining pentenes. The results are plotted in FIG. 1. From this data, it was confirmed that all of the alkaline earth metal ion-exchanged zeolites have higher activity compared to the parent ZSM-23, with the exception of 1.8 Mg/ZSM-23 (the material that had the highest Mg loading). For 1.8 Mg/ZSM-23, the loss in the acid concentration can explain the loss in activity compared to the other counterparts, yet the activity is on par with the parent ZSM-23.

Figure 2:
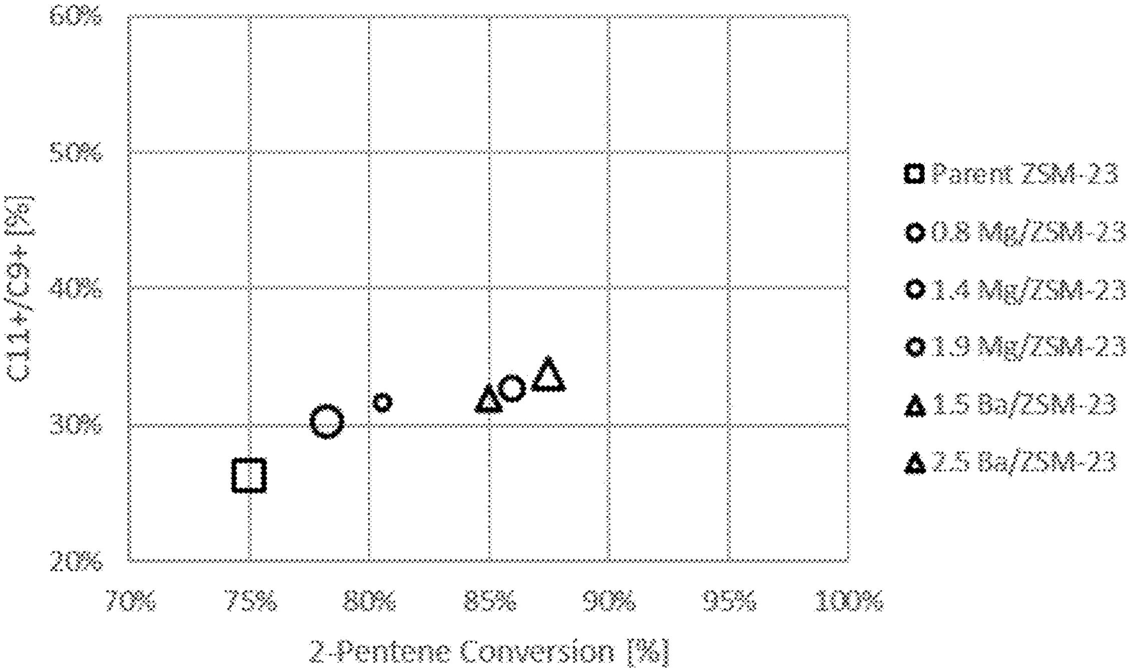
FIG. 2 shows distillate selectivity (molar ratio of $C_{11+}$ to $C_{9+}$) during oligomerization reactions using ZSM-23 catalysts with various amounts of alkaline earth metal ion exchange.

As a metric for selectivity to diesel, the desired product for this reaction, the C11+/C9+ molar ratio [%] was chosen. The conversion-selectivity plot for Mg/ZSM-23 is shown in FIG. 2. As shown in FIG. 2, Mg/ZSM-23 zeolites exhibit higher selectivities to higher molecular weight products compared to the parent ZSM-23 zeolite at between 70 to 80% conversion values. This result shows that through ion exchange, not only the activity but also the diesel selectivity can be improved simultaneously.

The increase in conversion with such low levels of ion exchange is unexpected. Additionally, it is also unexpected that the small but substantial amount of alkaline earth metal cations were able to improve the ratio of diesel to naphtha produced during the oligomerization.

Example 2—Ion-Exchanged ZSM-12

ZSM-12 crystals with small but substantial amounts of alkaline earth metal cations were formed according to the method from Example 5 in U.S. Pat. No. 6,893,624. To make ZSM-12, a mixture was prepared from 1204 g of water, 105 g of methyltriethylammonium Bromide (MTEABr), 283 g of sodium silicate solution, 16.8 g of aluminum nitrate and 16.45 of sulfuric acid (98% solution). The mixture bad the following molar composition: $SiO_2/Al_2O_3$=60; $H_2O/SiO_2$=57; OH/$SiO_2$=0.3; $Na^+/SiO_2$=0.6; MTEABr/$SiO_2$=0.4.

The mixture was reacted at 320° F. (160° C.) in a 2 liter autoclave with stirring at 150 RPM for 120 hours. The product was filtered, washed with deionized (DI) water and dried at 250° F. (120° C.). The XRD pattern of the as-synthesized material showed the typical pure phase of ZSM-12 topology. An SEM of the as-synthesized material showed that the material was composed of agglomerates of small crystals (with an average crystal size of about 0.05 microns).

The as-synthesized crystals were converted into the hydrogen form by two ion exchanges with ammonium nitrate solution at room temperature, followed by drying at 250° F. (120° C.) and calcination at 1000° F. (540° C.) for 6 hours. The crystals were then ion-exchanged to have a small but substantial content of alkaline earth metal.

Table 2 summarizes the composition, textual properties, and acid concentration of $M^{2+}$/ZSM-12 zeolites analyzed using ICP-AES, $N_2$ adsorption, and TPAD, respectively. For the ZSM-12 samples in Table 2, the degree of ion-exchange was somewhat greater than for the ZSM-23 zeolites shown in Table 1, as the $M^{2+}$/Al ratio in Table 2 varies between 4.2% and 16.2%. Similar to the results for ZSM-23, ion-exchange with the alkaline earth metal cations resulted in significant loss in the micropore volume was observed compared to the parent material (0.140 cc/g), indicating that the alkali earths are occupying the zeolite micropores. Despite micropore volume loss, the acid concentration was maintained between 0.530 and 0.540 mEq/g. The sample names were designated based on the type of alkali earth (Mg or Ba) and the $M^{2+}$/Al molar ratio in %. The designated names are also summarized in Table 2.

TABLE 2

Characterization of ZSM-12 Ion-Exchanged Samples

| Sample name | $M^{2+}$/Al | BET specific surface area [$m^2$/g] | Micropore volume [cc/g] | Ammonia desorbed [mEq/g] |
|---|---|---|---|---|
| Parent ZSM-12 | 0.000 | 400.8 | 0.140 | 0.549 |
| 8.3 Mg/ZSM-12 | 0.083 | 316.4 | 0.130 | 0.534 |
| 12.0 Mg/ZSM-12 | 0.120 | 363.8 | 0.127 | 0.533 |
| 16.2 Mg/ZSM-12 | 0.162 | 330.1 | 0.135 | 0.538 |
| 4.2 Ba/ZSM-12 | 0.042 | 329.2 | 0.135 | 0.537 |
| 7.1 Ba/ZSM-12 | 0.071 | 357.5 | 0.125 | 0.532 |

Figure 3:
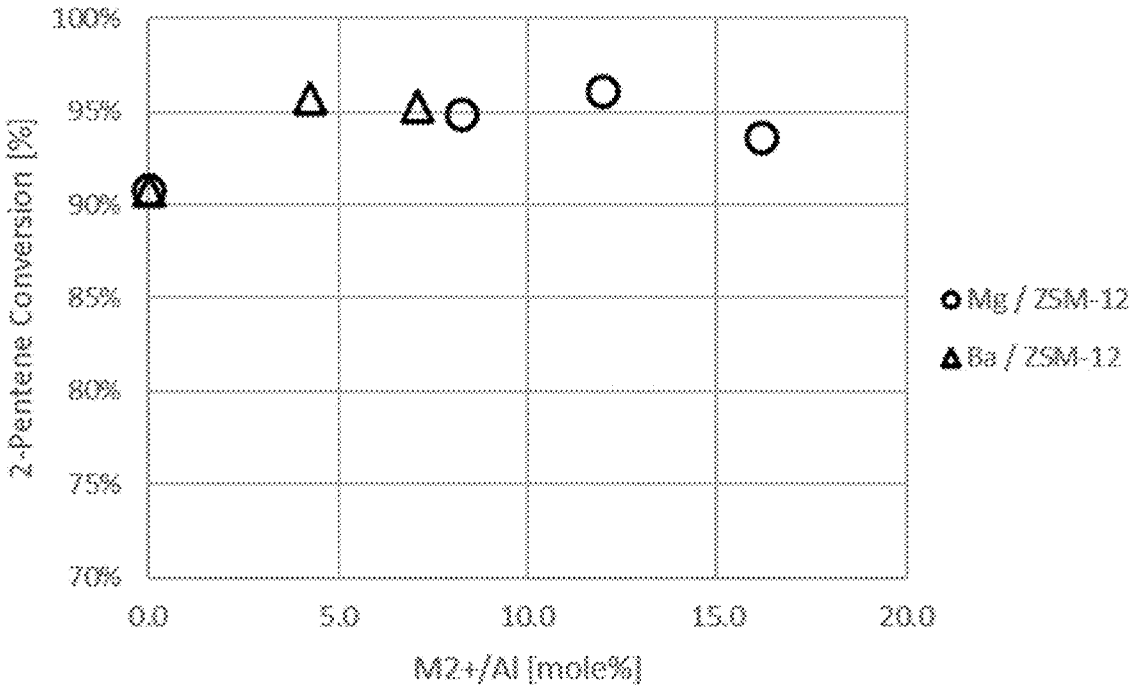
FIG. 3 shows olefin conversion during oligomerization reactions using ZSM-12 catalysts with various amounts of alkaline earth metal ion exchange.

The materials in Table 2 were tested for 2-pentene (2-C5=, cis and trans) oligomerization reaction in a batch reactor configuration. The conversion was calculated from the amount of remaining pentenes. The results are plotted in FIG. 3. From this data, it was confirmed that all of the zeolites have higher activity compared to the parent ZSM-12. It is noted that at the activity starts to trend back toward the parent activity at the highest level of Mg loading.

Figure 4:
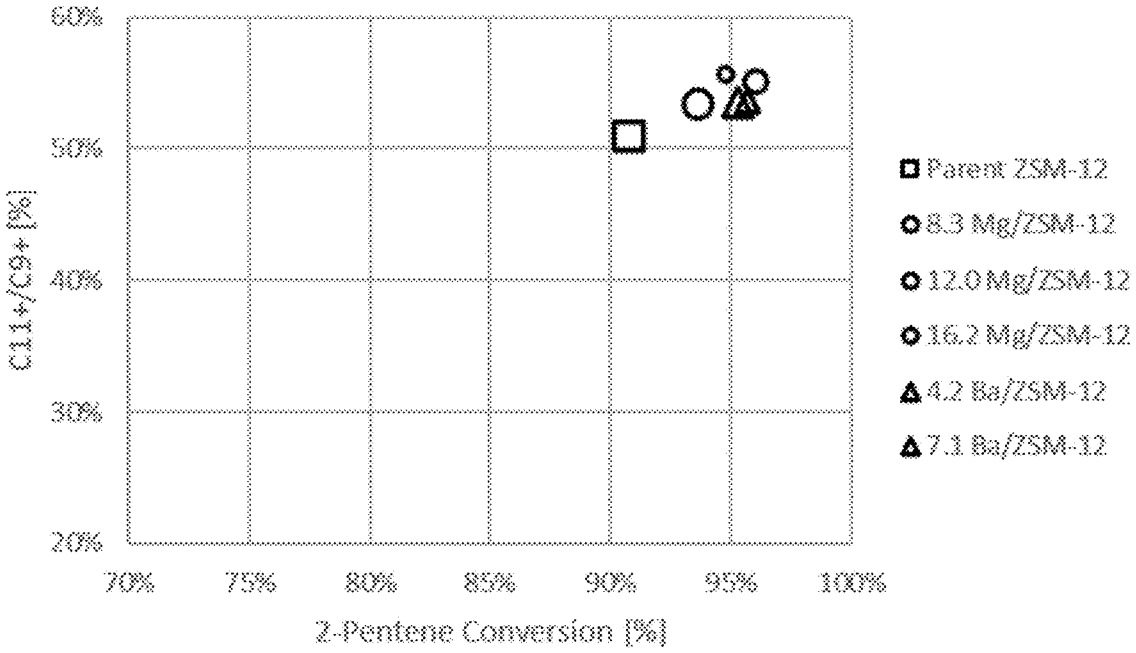
FIG. 4 shows distillate selectivity (molar ratio of $C_{11+}$ to $C_{9+}$) during oligomerization reactions using ZSM-12 catalysts with various amounts of alkaline earth metal ion exchange.

As a metric for selectivity to diesel, the desired product for this reaction, the C11+/C9+ molar ratio [%] was chosen. The conversion-selectivity plot for Mg/ZSM-12 and Ba/ZSM-12 is shown in FIG. 4. As shown in FIG. 4, Mg/ZSM-12 and Ba/ZSM-12 zeolites exhibit higher selectivities to higher molecular weight products compared to the parent ZSM-12 zeolite at conversion values near 90%. This result shows that through ion exchange, not only the activity but also the diesel selectivity can be improved simultaneously.

The ability to increase both activity and diesel selectivity with both Mg and Ba is unexpected. It is noted that for zeolites that are ion exchanged with alkali metals, prior studies have shown the potassium is not able to improve diesel selectivity.

Example 3—Ion-Exchanged ZSM-57

ZSM-57 crystals with small but substantial amounts of alkaline earth metal cations were formed according to the method in Example 8 of U.S. Pat. No. 4,873,067, which is incorporated herein by reference for the limited purpose of describing synthesis of ZSM-57.

Table 3 summarizes the composition, textual properties, and acid concentration of $M^{2+}$/ZSM-57 zeolites analyzed using ICP-AES, $N_2$ adsorption, and TPAD, respectively. For the ZSM-57 samples in Table 3, the degree of ion-exchange is small but still somewhat greater than for the ZSM-23 zeolites shown in Table 1. The $M^{2+}$/Al ratio in Table 3 varies between 1.6% and 5.1%. In contrast to the results for ZSM-23, for ZSM-57, ion-exchange with the alkaline earth cations did not substantially change the micropore volume compared to the parent material (0.140 cc/g), indicating that the alkali earths are occupying the zeolite micropores. However, the addition of barium resulted in some lowering of the acidity of the resulting ion-exchanged zeolite relative to the parent ZSM-57. The sample names were designated based on the type of alkali earth (Mg or Ba) and the $M^{2+}$/Al molar ratio in %. The designated names are also summarized in Table 3.

TABLE 3

Characterization of ZSM-57 Ion-Exchanged Samples

| Sample name | $M^{2+}$/Al | BET specific surface area [$m^2$/g] | Micropore volume [cc/g] | Ammonia desorbed [mEq/g] |
|---|---|---|---|---|
| Parent ZSM-57 | 0.000 | 363.0 | 0.167 | 0.664 |
| 1.6 Mg/ZSM-57 | 0.016 | 433.2 | 0.171 | 0.667 |
| 1.9 Mg/ZSM-57 | 0.019 | 479.2 | 0.170 | 0.655 |
| 2.2 Mg/ZSM-57 | 0.022 | 484.4 | 0.173 | 0.661 |
| 3.1 Ba/ZSM-57 | 0.031 | 408.9 | 0.167 | 0.625 |
| 5.1 Ba/ZSM-57 | 0.051 | 406.1 | 0.166 | 0.619 |

Figure 5:
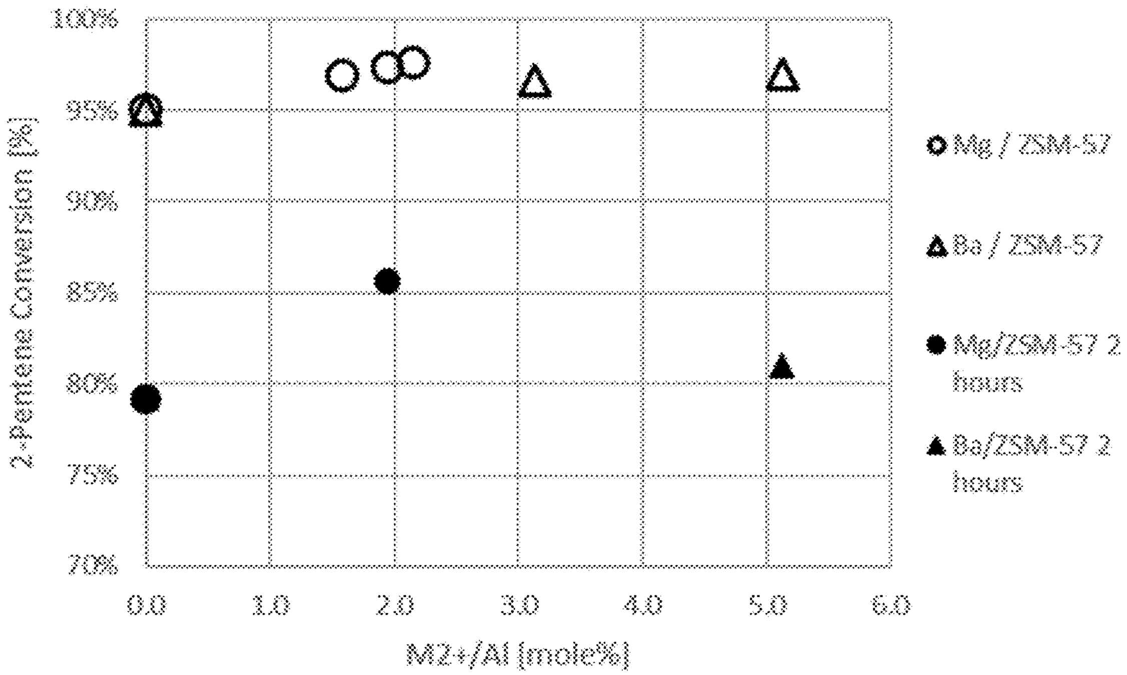
FIG. 5 shows olefin conversion during oligomerization reactions using ZSM-57 catalysts with various amounts of alkaline earth metal ion exchange.

The materials in Table 3 were tested for 2-pentene (2-C5=, cis and trans) oligomerization reaction in a batch reactor configuration. The conversion was calculated from the amount of remaining pentenes. The results are plotted in FIG. 5. From this data, it was confirmed that all of the alkaline earth metal ion-exchanged zeolites have higher activity compared to the parent ZSM-57. It is noted that after four hours, the conversion was above 95% for both parent and ion-exchanged ZSM-57 samples. The increase in activity is more apparent when a comparison is made after only two hours.

Figure 6:
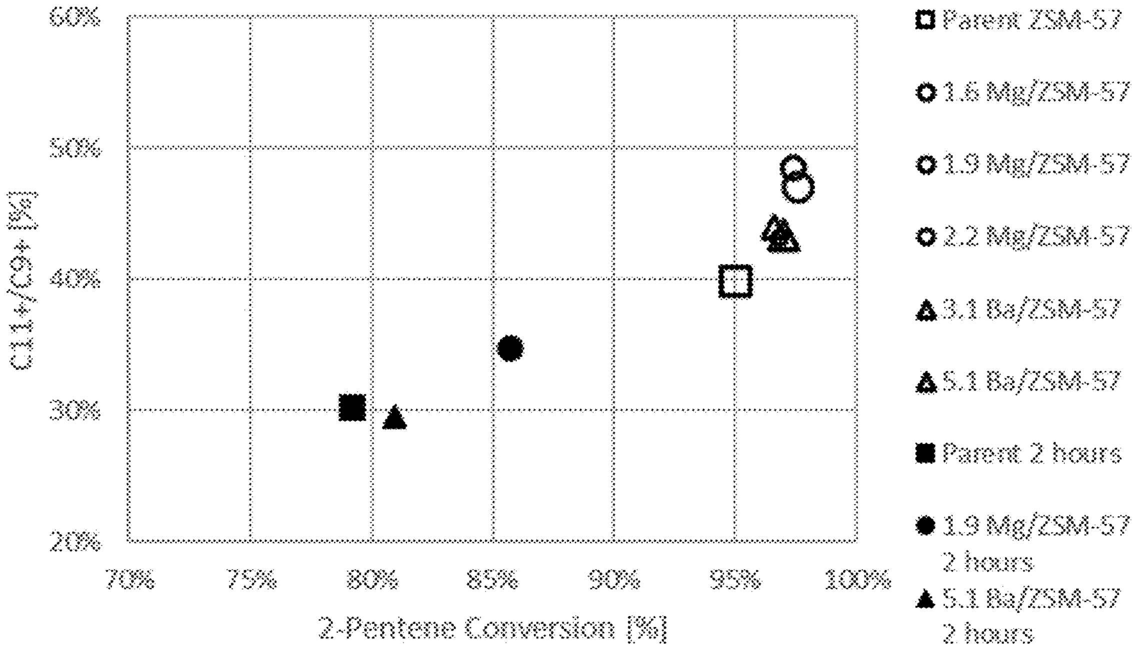
FIG. 6 shows distillate selectivity (molar ratio of $C_{11+}$ to $C_{9+}$) during oligomerization reactions using ZSM-57 catalysts with various amounts of alkaline earth metal ion exchange.

As a metric for selectivity to diesel, the desired product for this reaction, the C11+/C9+ molar ratio [%] was chosen. The conversion-selectivity plot for Mg/ZSM-57 and Ba/ZSM-57 is shown in FIG. 6. As shown in FIG. 6, Mg/ZSM-57 and Ba/ZSM-57 zeolites exhibit higher selectivities to higher molecular weight products compared to the parent ZSM-57 zeolite, with the exception of the data point for the highest amount of Ba loading at only two hours of conversion time. This result shows that through ion exchange, not only the activity but also the diesel selectivity can be improved simultaneously.

The ability to increase both activity and diesel selectivity with both Mg and Ba is unexpected. It is noted that for zeolites that are ion exchanged with alkali metals, prior studies have shown the potassium is not able to improve diesel selectivity.

Figure 7:
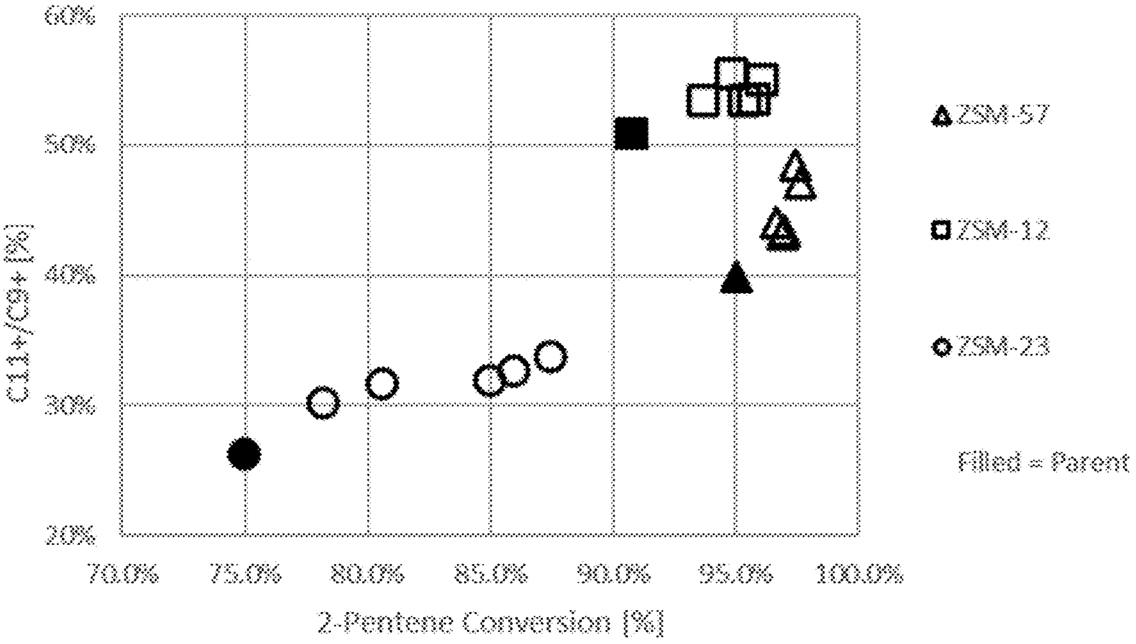
FIG. 7 shows olefin conversion results for ZSM-23, ZSM-12, and ZSM-57 catalysts with various amounts of alkaline earth metal ion exchange.

FIG. 7 displays the results from testing of ZSM-12, ZSM-23, and ZSM-57 into a single figure, to show the consistency of the improvement in activity across the various types of zeolites.

ADDITIONAL EMBODIMENTS

Embodiment 1. A method for oligomerizing olefins, comprising: exposing a feed comprising $C_2$ to $C_{12}$ olefins to an oligomerization catalyst comprising an alkaline earth metal ion-exchanged zeolitic framework material under oligomerization conditions to form an oligomerized effluent comprising a diesel boiling range fraction, wherein the alkaline earth metal ion-exchanged zeolitic framework material comprises silica and alumina, the alkaline earth metal ion-exchanged zeolitic framework material comprising a molar ratio of alkaline earth metals to aluminum of 0.005 to 0.2, and wherein the alkaline earth metal ion-exchanged zeolitic framework material comprises a 10-member ring zeolitic framework structure, a 1-D 12-member ring zeolitic framework structure, or a combination thereof, the oligomerization catalyst optionally further comprising a binder.

Embodiment 2. The method of Embodiment 1, wherein the alkaline earth metal ion-exchanged zeolitic framework material comprises a molar ratio of alkaline earth metals to aluminum of 0.005 to 0.08.

Embodiment 3. The method of Embodiment 1 or 2, wherein the alkaline earth metal ion-exchanged zeolitic framework material comprises a molar ratio of alkaline earth metals to aluminum of 0.005 to 0.05.

Embodiment 4. The method of any of the above embodiments, wherein the alkaline earth metal ion-exchanged zeolitic framework material comprises a molar ratio of alkaline earth metals to aluminum of 0.005 to 0.02.

Embodiment 5. The method of any of the above embodiments, wherein the alkaline earth metal ion-exchanged zeolitic framework material comprises a molar ratio of silica to alumina of 100 or less, the molar ratio of silica to alumina optionally being 10 to 70.

Embodiment 6. The method of any of the above embodiments, wherein the alkaline earth ion-exchanged zeolitic framework material comprises a 1-D zeolitic framework structure.

Embodiment 7. The method of Embodiment 6, wherein the alkaline earth metal ion-exchanged zeolitic framework material comprises an MTT framework structure, an MTW framework structure, an *MRE framework structure, or a combination thereof.

Embodiment 8. The method of any of the above embodiments, wherein the alkaline earth metal ion-exchanged zeolitic material comprises a 2-D, 10-member ring zeolitic framework structure, a 3-D, 10-member ring zeolitic framework structure, or a combination thereof.

Embodiment 9. The method of Embodiment 8, wherein the alkaline earth metal ion-exchanged zeolitic framework material comprises an FER framework structure, an MFS framework structure, an MFI framework structure, an MEL framework structure, or a combination thereof.

Embodiment 10. The method of any of Embodiments 6-9, wherein the alkaline earth metal ion-exchanged zeolitic framework material comprises an intergrowth material.

Embodiment 11. The method of any of the above embodiments, wherein the alkaline earth metal ion-exchanged zeolitic framework material comprising a pore size of 4.5 Angstroms to 8.0 Angstroms.

Embodiment 12. The method of any of the above embodiments, wherein the alkaline earth metals comprise Mg, Ca, Sr, Ba, or a combination thereof, optionally Mg, Ba, or a combination thereof.

Embodiment 13. The method of any of the above embodiments, wherein the feed comprises a weight ratio of alkenes to alkanes between 10:90 and 90:10.

Embodiment 14. The method of any of the above embodiments, wherein the feed comprises $C_2$-$C_6$ alkenes.

Embodiment 15. The method of Embodiment 14, wherein the feed further comprises $C_2$-$C_6$ alkanes, the feed having a weight ratio of $C_2$-$C_6$ alkenes to $C_2$-$C_6$ alkanes between 10:90 and 90:10.

While the present invention has been described and illustrated by reference to particular embodiments, those of ordinary skill in the art will appreciate that the invention lends itself to variations not necessarily illustrated herein. It will also be apparent to those skilled in the art that when numerical lower limits and numerical upper limits are listed herein, ranges from any lower limit to any upper limit are contemplated. Also, all numerical values within the detailed description herein are modified by "about" the indicated value, and take into account experimental error and variations that would be expected by a person having ordinary skill in the art. Where in the foregoing description, integers or elements are mentioned which have known, obvious or foreseeable equivalents, then such equivalents are herein incorporated as if individually set forth. For these reasons, then, reference should be made solely to the appended claims for purposes of determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments.

What is claimed is:

1. A method for oligomerizing olefins, comprising:
   exposing a feed comprising $C_2$ to $C_{12}$ olefins to an oligomerization catalyst comprising an alkaline earth metal ion-exchanged zeolitic framework material under oligomerization conditions to form an oligomerized effluent comprising a diesel boiling range fraction,
   wherein the alkaline earth metal ion-exchanged zeolitic framework material comprises silica and alumina, the alkaline earth metal ion-exchanged zeolitic framework material comprising a molar ratio of alkaline earth metals to aluminum of 0.005 to 0.08, and
   wherein the alkaline earth metal ion-exchanged zeolitic framework material comprises a 10-member ring zeolitic framework structure, a 1-D 12-member ring zeolitic framework structure, or a combination thereof.

2. The method of claim 1, wherein the alkaline earth metal ion-exchanged zeolitic framework material comprises a molar ratio of alkaline earth metals to aluminum of 0.005 to 0.05.

3. The method of claim 1, wherein the alkaline earth metal ion-exchanged zeolitic framework material comprises a molar ratio of alkaline earth metals to aluminum of 0.005 to 0.02.

4. The method of claim 1, wherein the alkaline earth metal ion-exchanged zeolitic framework material comprises a molar ratio of silica to alumina of 100 or less.

5. The method of claim 4, wherein the alkaline earth metal ion-exchanged zeolitic framework material comprises a molar ratio of silica to alumina of 10 to 70.

6. The method of claim 1, wherein the alkaline earth metal ion-exchanged zeolitic framework material comprises a 1-D zeolitic framework structure.

7. The method of claim 6, wherein the alkaline earth metal ion-exchanged zeolitic framework material comprises an MTT framework structure, an MTW framework structure, an *MRE framework structure, or a combination thereof.

8. The method of claim 6, wherein the alkaline earth metal ion-exchanged zeolitic framework material comprises an intergrowth material.

9. The method of claim 1, wherein the alkaline earth metal ion-exchanged zeolitic material comprises a 2-D, 10-member ring zeolitic framework structure, a 3-D, 10-member ring zeolitic framework structure, or a combination thereof.

10. The method of claim 9, wherein the alkaline earth metal ion-exchanged zeolitic framework material comprises an FER framework structure, an MFS framework structure, an MFI framework structure, an MEL framework structure, or a combination thereof.

11. The method of claim 9, wherein the alkaline earth metal ion-exchanged zeolitic framework material comprises an intergrowth material.

12. The method of claim 1, wherein the alkaline earth metal ion-exchanged zeolitic framework material comprising a pore size of 4.5 Angstroms to 6.0 Angstroms.

13. The method of claim 1, wherein the alkaline earth metals comprise Mg, Ca, Sr, Ba, or a combination thereof.

14. The method of claim 1, wherein the alkaline earth metals comprise Mg, Ba, or a combination thereof.

15. The method of claim 1, wherein the feed comprises a weight ratio of alkenes to alkanes between 10:90 and 90:10.

16. The method of claim 1, wherein the feed comprises $C_2$-$C_6$ alkenes.

17. The method of claim 1, wherein the feed further comprises $C_2$-$C_6$ alkanes, the feed having a weight ratio of $C_2$-$C_6$ alkenes to $C_2$-$C_6$ alkanes between 10:90 and 90:10.

18. The method of claim 1, wherein the oligomerization catalyst further comprises a binder.

* * * * *